US00PP34002P2

(12) United States Plant Patent
Van Swieten

(10) Patent No.: US PP34,002 P2
(45) Date of Patent: Mar. 8, 2022

(54) ***PHALAENOPSIS* ORCHID PLANT NAMED 'PHA1324166'**

(50) Latin Name: ***Phalaenopsis* hybrid**
Varietal Denomination: PHA1324166

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,578

(22) Filed: Aug. 25, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

CPVO Application on a UPOV filing for a *Phalaenopsis* plant named, 'PHA1324166', having application No. 20202305 filed Sep. 22, 2020.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHA1324166', particularly characterized by having reddish-purple, striped, and edged flowers with extra-large and reddish-purple lips, flowers that are concave in lateral view, leaves with a striped pattern, and is propagated by meristem tissue culture, is disclosed.

3 Drawing Sheets

Genus and species: *Phalaenopsis* hybrid.
Variety denomination: 'PHA1324166'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1324166'.

The new *Phalaenopsis* plant is a product of a planned breeding program conducted by the inventor in Bleiswijk, the Netherlands. The objective of this breeding program was to create a new *Phalaenopsis* plant with numerous attractive and small, reddish-purple, striped, and edged flowers with extra-large reddish-purple lips, suitable for potted plant production.

The new *Phalaenopsis* plant 'PHA1324166' is a result of cross-pollination made by the inventor in March 2013 in Bleiswijk, the Netherlands, of the proprietary female, or seed parent, *Phalaenopsis* hybrid '44473-011' (unpatented) with the proprietary male, or pollen parent, *Phalaenopsis* hybrid 'PHALDIMXAP' (U.S. Plant Pat. No. 25,294).

The new *Phalaenopsis* was selected by the inventor as a single plant within the progeny of the stated cross-pollination in a controlled greenhouse in Bleiswijk, the Netherlands, in December 2015. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2305), by Applicant who obtained the subject matter disclosed directly from the inventor. 'PHA1324166' has not been made publicly available or sold anywhere in the world prior to the effective filing date of this application with the exception of sales or disclosures made one year or less before the effective filing date of this claimed invention by Applicant who obtained 'PHA1324166' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1324166' as a new and distinct variety of *Phalaenopsis* plant:

1) Reddish-purple, striped, and edged flowers;
2) Flowers have extra-large and reddish-purple lips;
3) Flower shape in lateral view is concave; and
4) Leaf pattern is striped.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2021. Colors in the photographs may differ from the color values cited in the detailed botanical description, which accurately describe the actual colors of the new variety.

DESCRIPTION OF THE NEW VARIETY

Figure 1:
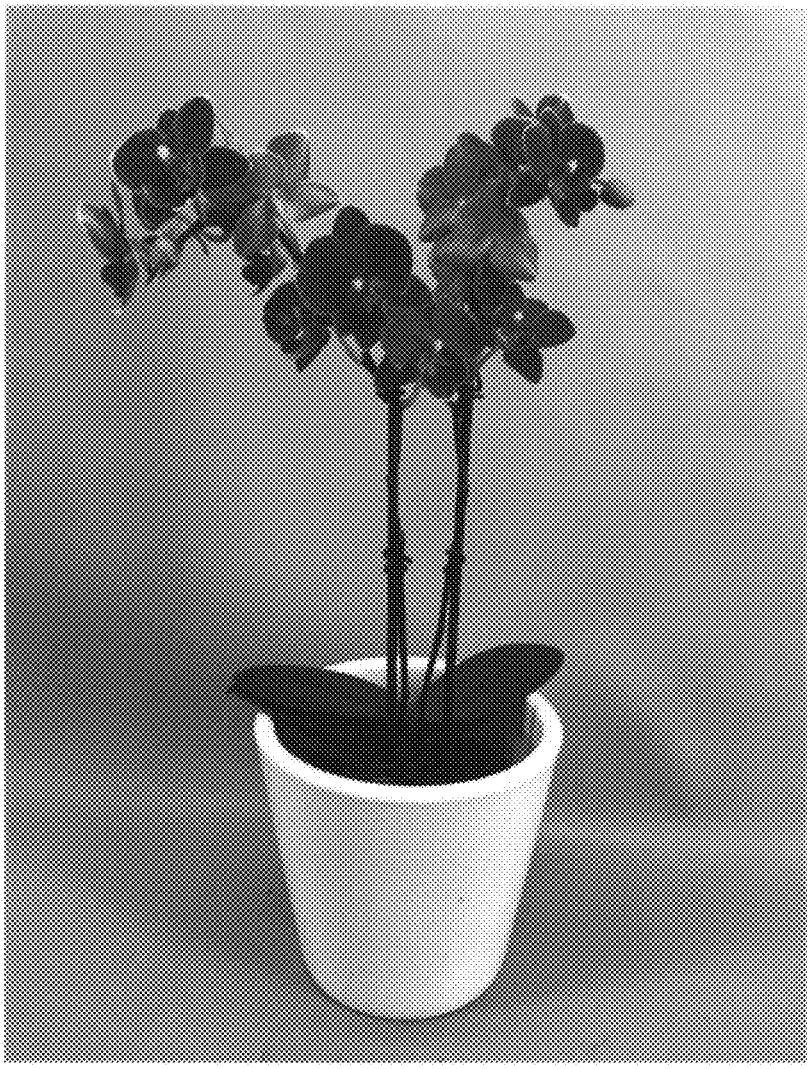
FIG. 1 shows the overall plant habit, including blooms, buds, and foliage of 'PHA1324166'.
Figure 2:
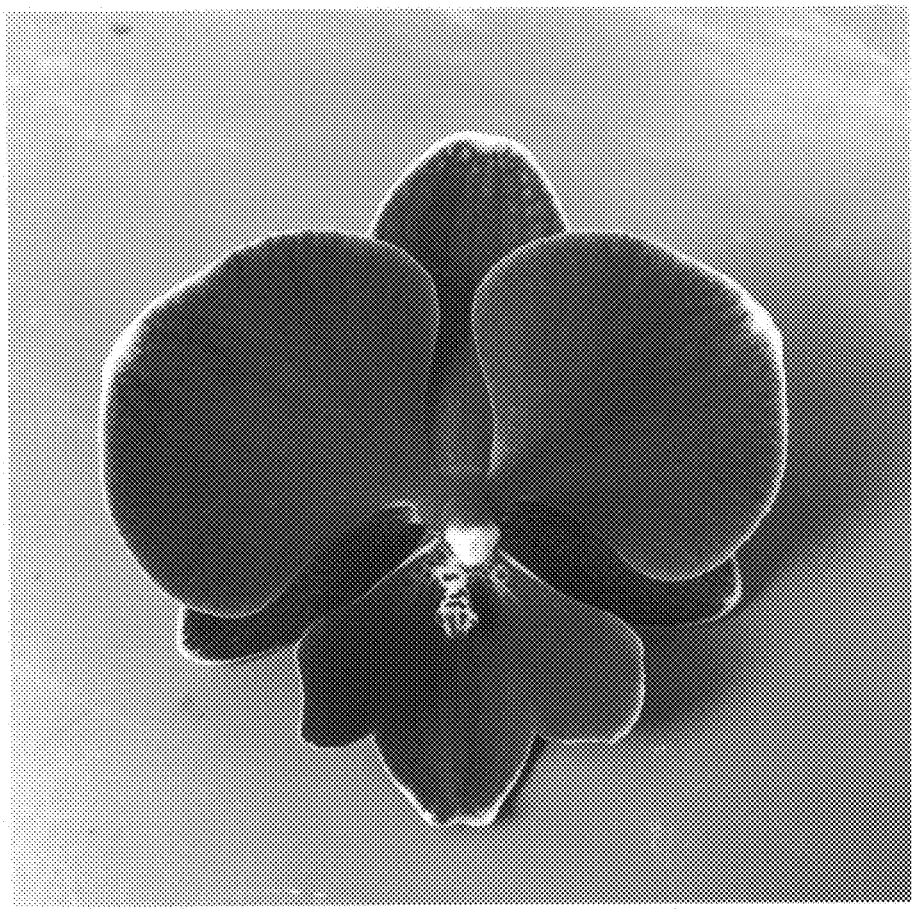
FIG. 2 shows a close-up of a flower of 'PHA1324166'.
Figure 3:
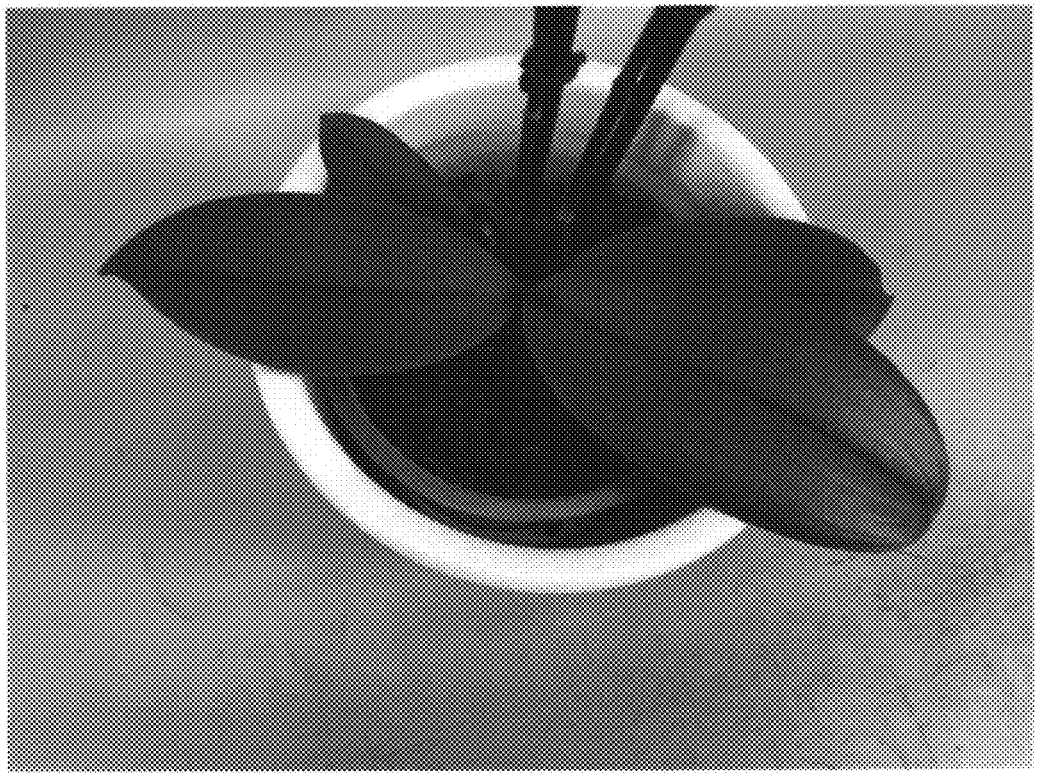
FIG. 3 shows an overhead view of the leaves of 'PHA1324166'.

The following detailed description sets forth the distinctive characteristics of 'PHA1324166'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1324166'.

Parentage:

*Female parent*.—*Phalaenopsis* cultivar '44473-011' (unpatented).

*Male parent*.—*Phalaenopsis* cultivar 'PHALDIMXAP' (U.S. Plant Pat. No. 25,294).

Propagation:

*Type*.—Meristem tissue culture.

Roots:

*Root description*.—Greyed-green (a color in between RHS 190B and RHS 190C) colored roots with branching lateral roots having yellowish-green (RHS N144A) with a touch of purple (RHS N77A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height (from soil level to top of inflorescence)*.—Approximately 30.0 cm to 35.0 cm.

*Width (measured from leaf tips)*.—About 20.0 cm to 23.0 cm.

*Vigor*.—Strong.

Leaves:

*Mature leaves*.—Quantity per plant: 5 to 7 leaves are produced before flowering. Length (fully expanded): 9.0 cm to 12.0 cm. Width: 4.5 cm to 5.5 cm. Position of the broadest part of the leaf: At the middle. Shape: Narrow oblong. Base shape: Slightly to moderately elongated. Apex: Obtuse asymmetric. Leaf blade angle with the petiole (measured from the horizontal position): Between 5 degrees and 20 degrees. Leaf margin: Entire. Color: Upper surface: Green (RHS 146A) with a touch of purple (RHS N77A) at the base; darker green (RHS 147A) with a touch of purple (RHS N77A) toward the tip; diluting green (RHS 147A) with a touch of purple stripes (RHS N77A). Lower surface: Mix of dark purplish-red (RHS N79A) and green (RHS 147C); dark yellowish-brown margin (RHS N199B). Texture (both upper and lower surfaces): Smooth. Thickness: 2.0 mm to 3 0 mm. Variegation: Absent. Venation: Pattern: Parallel. Color of the midvein: Upper surface: RHS N77A. Lower surface: RHS 200A.

Peduncle:

*Quantity per plant*.—1 to 2.

*Number of flowers per peduncle*.—10 to 15.

*Length*.—30.0 cm to 35.0 cm.

*Diameter*.—3.0 mm to 4.0 mm.

*Strength*.—Strong.

*Aspect*.—Upright to slightly pendent.

*Texture*.—Smooth.

*Color*.—Dark reddish-brown (RHS 200A) with a touch of green (RHS 147C).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 140.0 mm to 230.0 mm.

*Flowering time*.—First flowers can be expected 10 to 11 months after planting in a 12-cm pot.

*Flower*.—Height: 50.0 mm to 55.0 mm. Diameter: 50.0 mm to 55.0 mm. Depth of lip: 22.0 mm to 24.0 mm.

*Flower shape*.—Concave.

*Flower longevity*.—On the plant: 16 to 18 weeks.

*Fragrance*.—Absent.

*Flower bud*.—Average size: Medium. Length: 17.0 min. to 19.0 mm. Width: 16.0 mm to 18.0 mm. Shape: Egg shaped. Color: Yellow-green (a color in between RHS 146D and RHS 144C) with a purplish-red overcolor (RHS N77B).

*Petals*.—Arrangement: Open/free. Shape: Semi-circular. Apex: Obtuse asymmetric. Margin: Entire. Length (from base to tip): 23.0 mm to 25.0 mm. Width: 28.0 mm to 30.0 mm. Position of the broadest part of the petal: Toward the base. Color (when fully opened): Upper surface: Basic color: Reddish-purple (RHS N78A). Over color: Dark purplish-red stripes (RHS N79C) and white edge (RHS NN155C). Lower surface: Basic color: Reddish-purple (RHS N78B). Over color: Light purple (RHS 76A) at the middle from base toward the tip. Number of spots and stripes on the petals (upper surface): Medium to many stripes. Color of spots and stripes on the petals (upper surface): RHS N79C. Density of netting of the petals (upper surface): None. Color of the netting (upper surface): None.

*Dorsal sepal*.—Shape: Elliptic. Apex: Emarginated symmetric. Margin: Entire. Length (from base to tip): 25.0 mm to 27.0 mm. Width: 16.0 mm to 18.0 mm. Position of the broadest part of the dorsal sepals: At the middle. Color (when fully opened): Upper surface: Basic color: Reddish-purple (RHS N78A). Over color: Dark purplish-red stripes and netting (RHS N79C); white edge (RHS NN155C). Lower surface: Basic color: Light yellow-green (RHS 196C). Over color: Purplish-pink (RHS N78C) toward margins. Number of spots and stripes on the dorsal sepals (upper surface): Medium stripes. Color of spots and stripes on the dorsal sepals (upper surface): RHS N79C. Density of netting of the dorsal sepals (upper surface): Medium. Color of the netting (upper surface): RHS N79C.

*Lateral sepals*.—Shape: Ovate. Apex: Obtuse asymmetric. Margin: Entire. Length (from base to tip): 25.0 mm to 27.0 mm. Width: 14.0 mm to 16.0 mm. Position of the broadest part of the lateral sepals: Toward the base. Color (when fully opened): Upper surface: Basic color: Reddish-purple (RHS N78A). Over color: Light yellow-green (RHS 145D) and dotted (a color in between RHS N79B and RHS N79C) at the base; dark reddish-purple stripes and netting (RHS N79C); white edge (RHS NN155C). Lower surface: Basic color: Yellow-green (RHS 145C). Over color: Purplish-pink (RHS N78C) toward margins and white edge (RHS NN155C). Number of spots, dots, and stripes on the lateral sepals (upper surface): Few to medium dots; medium stripes. Color of spots, dots, and stripes on the lateral sepals (upper surface): Dots (a color in between RHS N79B and RHS N79C); stripes (RHS N79C). Density of netting of the lateral sepals (upper surface): High. Color of the netting (upper surface): RHS N79C.

*Labellum* (*lip*).—Whiskers: Present, but very short. Length of whiskers: 1.0 mm to 3.0 mm. Color of whiskers: White (RHS NN155C). Pubescence on the lip: Absent.

*Lateral lobe*.—Shape: Not applicable. Margin: Slightly undulated. Length: 20.0 mm to 22.0 mm. Width: 8.0 mm to 10.0 mm. Color: Upper surface: Hint of very light purple (RHS 76B) with few dots (RHS 59B) at the base; reddish-purple (RHS N78A) toward the tip; white edge (RHS NN155C). Lower surface: Light purple (RHS 76A) at the base; reddish-purple (RHS N78B) toward the tip. Number of spots, dots, and stripes on the lateral lobe: Few dots. Color of spots, dots, and stripes on the lateral lobe: RHS 59B. Density of netting of the lateral lobe: None. Color of the netting: None.

*Apical lobe*.—Shape: Trapezoid. Margin: Entire. Length: 7.0 mm to 9.0 mm. Width: 12.0 mm to 14.0 mm. Color: Upper surface: Reddish-purple (RHS N78A); dark purplish-red stripes (RHS N79C); white margin (RHS NN155C) toward whiskers. Lower surface: Very light purple (RHS 76B) at the middle, from base toward whiskers; reddish-purple (RHS N78B) toward margins and whiskers. Number of spots and stripes on the apical lobe: Few stripes. Color of spots and stripes on the apical lobe: RHS N79C. Density of netting of the apical lobe: None. Color of the netting: None.

*Callus*.—Average size: Small. Height: 4.0 mm to 5.0 mm. Length: 2.0 mm to 3.0 mm. Color: White (RHS NN155C); dotted (RHS N78A).

Reproductive organs:

*Column*.—Length: 8.0 mm to 10 0 mm. Diameter: 3.0 mm to 4.0 mm. Color: Reddish-purple (RHS N78A).

*Pollinia*.—Quantity: 2. Diameter: 0.8 mm to 1.0 mm. Color: Orange-yellow (RHS 21A).

*Ovary*.—Length: 12.0 mm to 14.0 mm. Diameter: 2.0 mm to 2.3 mm.

*Pedicel*.—Length: 32.0 mm to 34.0 mm. Diameter: 2.4 mm to 2.7 mm. Color: Light yellow-green (RHS 145C) and lighter yellow-green (RHS 145D) with a touch of very light purple (RHS 76C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1324166' differs from the female parent plant '44473-011' (unpatented) in that 'PHA1324166' has obtuse petal apexes, emarginated dorsal sepal apexes, flowers with a basic color of reddish-purple, and apical lobes with a main color of reddish-purple, whereas '44473-011' has slightly emarginated petal apexes, obtuse dorsal sepal apexes, flowers with a main color of light reddish-purple, and apical lobes with a main color of light reddish-purple.

'PHA1324166' differs from the male parent plant 'PHALDIMXAP' (U.S. Plant Pat. No. 25,294) in that 'PHA1324166' has flowers with a striped and edged pattern and an extra-large lip size, whereas 'PHALDIMXAP' has flowers with a center pattern and a normal lip size.

'PHA1324166' is most similar to the commercial *Phalaenopsis* plants named 'PHALFATYMO' (U.S. Plant Pat. No. 32,478) and 'PHALFEMYM' (U.S. Plant Pat. No. 29,783). 'PHA1324166' differs from the commercial variety 'PHALFATYMO' in that 'PHA1324166' has trapezoid apical lobes, white whiskers, calluses with a main color of white, and an extra-large lip size, whereas 'PHALFATYMO' has broad ovate apical lobes, dark purplish-red whiskers, calluses with a main color of light greenish-yellow, and a normal lip size. Additionally, 'PHA1324166' has larger flowers than 'PHALFATYMO'.

'PHA1324166' differs from the commercial variety 'PHALFEMYM' in that 'PHA1324166' has trapezoid apical lobes, calluses with a main color of white, and an extra-large lip size, whereas 'PHALFEMYM' has ovate apical lobes, calluses with a main color of yellow, and a normal lip size. Additionally, 'PHA1324166' has narrower leaves than 'PHALFEMYM'.

I claim:

1. A new and distinct variety of *Phalaenopsis* plant named 'PHA1324166', substantially as described and illustrated herein.

* * * * *